United States Patent [19]

Weiss

[11] Patent Number: 4,816,964
[45] Date of Patent: Mar. 28, 1989

[54] ADJUSTABLE, CONDUCTIVE BODY STRAP

[75] Inventor: John W. Weiss, St. Paul, Minn.

[73] Assignee: Minnesota Mining and Manufacturing Company, St. Paul, Minn.

[21] Appl. No.: 134,819

[22] Filed: Dec. 18, 1987

Related U.S. Application Data

[63] Continuation-in-part of Ser. No. 37,616, Apr. 13, 1987, Pat. No. 4,720,765.

[51] Int. Cl.⁴ ............................................. H05F 3/02
[52] U.S. Cl. .................................................... 361/220
[58] Field of Search ................ 361/212, 220, 223; 24/265 C, 265 WS, 519, 271, 198, 169

[56] References Cited

U.S. PATENT DOCUMENTS

| | | | |
|---|---|---|---|
| 3,015,754 | 1/1962 | Legge | 361/220 X |
| 3,063,447 | 11/1962 | Kirsten | 361/220 X |
| 3,857,397 | 12/1974 | Brosseau | 361/220 X |
| 4,038,726 | 8/1977 | Takahayashi | 24/198 |
| 4,077,091 | 3/1978 | Liljedahl | 24/198 X |
| 4,373,175 | 2/1983 | Mykkanen | 361/220 |
| 4,398,277 | 8/1983 | Christiansen et al. | 361/220 |
| 4,402,560 | 9/1983 | Swainbank | 439/37 |
| 4,459,633 | 7/1984 | Vandermark | 361/220 |
| 4,475,141 | 10/1984 | Antonevich | 361/220 |
| 4,540,271 | 9/1985 | Rakov | 361/220 X |
| 4,577,256 | 3/1986 | Breidegam | 361/220 |
| 4,596,053 | 6/1986 | Cohen et al. | 361/212 X |
| 4,676,561 | 1/1987 | Barrett, II | 361/220 X |
| 4,720,765 | 1/1988 | Weiss | 361/220 |

Primary Examiner—L. T. Hix
Assistant Examiner—Brian W. Brown
Attorney, Agent, or Firm—Donald M. Sell; William D. Bauer

[57] ABSTRACT

An adjustable, conductive body strap utilizing a connector securing a strip of material held in a closed loop with a mechanical connector with the interior surface of the strip of material being electrically conductive. An electrical connector connects the conductive surface of the strip of material to a connection point to provide for external electrical ground connection. The mechanical connector secures one end of the strip of material in place. The mechanical connector is formed from an electrically insulative outer piece and an electrically conductive inner piece which has a slot through which the opposite end of the strip of material which is adjustably secured back on itself intermediate the mechanical connector.

4 Claims, 3 Drawing Sheets

ADJUSTABLE, CONDUCTIVE BODY STRAP

RELATED APPLICATIONS

The present application is a continuation-in-part of U.S. Ser. No. 07/037,616, John Walter Weiss, Adjustable, Conductive, Body Strap, filed Apr. 13, 1987 now U.S. Pat. No. 4,720,765.

BACKGROUND OF THE INVENTION

The present invention relates generally to electrically conductive body straps and more particularly to electrically conductive body straps which are adjustable.

The buildup of electrostatic charges and their subsequent discharge is a significant problem in certain industries. Individuals working in an everyday work environment commonly may develop thousands of volts of electrostatic charge potential by, as an example, walking across carpeting or moving dissimilar objects against each other. An individual, or object, so charged presents a severe hazard in certain environments. One example is an explosive environment where the danger is inherently obvious. Another example is the electronic integrated circuit (component) industry. The charged individual or object may discharge near or through an electrostatic sensitive electronic component. For example, an individual who is electrostatically charged may hold an electrostatic sensitive component and then lay the component on a surface, e.g., a grounded work surface, at a different potential from the the individual. At the instant of contact, a potential difference of thousands of volts exists across the component, from the electrostatically charged individual to the grounded work surface. The current passing through or near, due to the electric field generated, may damage the component. The damage caused to the component may cause it to fail immediately or, worse, could degrade the operating characteristics or the reliability of the component. The result is either expensive rework or, worse, the existence of substandard or subreliable equipment in the field.

A device which is used to help control the electrostatic charge buildup on a person is a body strap or wrist strap to be worn by the individual. The body straps are conductive on the surface contacting the skin surface and provide for an electrical connection point. An electrical ground cord may then be connected to the strap connecting the strap to an electrical ground potential, preferably through a predetermined limiting resistance usually built into the connector or the cord itself. So connected, such a body strap operates by draining any accumulated electrostatic charge on the individual to ground before the electrostatic charge buildup reaches dangerous levels.

One prior art body strap is described in U.S. Pat. No. 4,398,277, Christiansen et al, Conductive Elastomeric Body Strap, which is hereby incorporated by reference. Christiansen et al. describes a body strap which is constructed from a band of fabric formed into a closed loop to encircle a body part, e.g., wrist, to which it is to be connected. The fabric is electrically conductive on the interior surface of the closed loop contacting the skin. A mechanical connection mechanism holds the loop of fabric in a fixed predetermined size. An electrical connection mechanism provides for an electrical connection between the conductive inner surface of the fabric to an electrical grounding cord which may be attached to the strap. The fabric is elastomeric to enable the body strap to expand to slip over the hand and still be snug around the wrist.

In the body strap described in Christiansen et al, the opposite ends of the fabric are permanently secured in the mechanical connector. The body of the connector has projections which grip the fabric and hold the fabric in the connector when the cover is secured. Thus, the resultant body strap formed is a fixed closed loop size. Since the fabric has a limit on the degree of its elastic nature, a range of sizes of closed loops for the body strap must be provided. This results in the necessity of stocking a plurality of differing sizes of body straps. Further, the elastomeric characteristics of the fabric generally means a fixed "life" of use of the fabric before its elastomeric or electroconductivity characteristics begin to break down. Since the fabric is secured in the connector at the factory, the replacement of the fabric requires replacement of the entire body strap.

The Charge-Guard 2200 series of static control wrist straps manufactured by Minn. Mining and Manufacturing Company, St. Paul, Minnesota and marketed by Static Control Systems/3M, Austin, Tex. is constructed generally as described in Christiansen et al. (Charge-Guard is a registered trademark of Minnesota Mining and Manufacturing Company, St. Paul, Minn.). In the Charge-Guard static control wrist straps, the ends of the projections 32, in Christiansen et al, are sonically welded after the fabric is in place to "mushroom" the ends of the projections in order to ensure that the fabric is secured in the connector.

U.S. Pat. No. 4,577,256, Breidegam, Woven Stretchable Grounding Strap, describes a wrist strap designed to be used to control electrostatic charge accumulations. The Breidegam strap has a clasp which allows its size to be adjusted. The adjustable clasp avoids the need to manufacture two or more models of the strap for different sized wrists. This does require that the strap be individually adjusted to fit snugly around the wrist of the individual wearer. If inadvertently or intentionally maladjusted, proper electrostatic protection may not be achieved. In the Breidegam strap, one end of the fabric is permanently secured into the clasp and held by plate and a rivet. Thus, one end of the fabric is fixed at the factory for the entire life of the strap. The second end of the fabric is engaged in the clasp by a pivotally mounted gate which when closed "jams" the fabric holding it in place, optionally with teeth to help the securing of the fabric. Typically, a pivotally mounted "jam" or "wedge" as is described in Breidegam is referred to as an "over-center" device. These devices operate by wedging the fabric between the jam member and a reaction member by using an eccentric pivot with a relatively long jam operating lever to gain the necessary leverage for the jam to work. One problem in a strap as described in Breidegam is that it does not allow for full 360 degree electrical contact with the skin and the fabric is electrically only connected at one end. Since electrical contact is only provided to the external ground cord from the one fixed end of the fabric, any charge contacting the inner surface of the fabric must travel around the strap in one direction only until reaching the fixed end. This requires, in some instances, a charge must follow only one path to travel almost entirely around the fabric before being connected to a ground strap. Since the electrical conductivity of the fabric, due to its elasticity, is typically the weakest link in a wrist strap grounding system, along with the fabric to skin contact, such one way only conductivity is a serious problem. Another problem with the Breidegam strap is that the pivotally mounted gate does not lend itself to economical manufacture. Because of the forces involved, the pivot points are required to be quite sturdily built.

SUMMARY OF THE INVENTION

The present invention provides a body or wrist strap useful for the control of electrostatic charge accumulation. The body strap provides adjustability without the use of expensive "over-center" jam mechanisms. The body strap provides near full 360 degree electrical contact with the skin and two parallel paths to ground, provides easy readily readjustable sizing by the individual user or users and, because no free end of the fabric is exposed the possibility of having the electrically conductive inner surface of the fabric exposed is eliminated.

Thus, the present invention provides an adjustable, conductive body strap. The strap has a strip of material having a first end and a second end with the strip of material being electrically conductive on at least one surface, being elastomerically extensible in its longitudinal direction and being of at least a length to enable the strip of material to encircle a body part. A mechanical connector is formed from an electrically insulative outer piece and an electrically conductive inner piece, the pieces being secured together. The mechanical connector receives the first end and the second end of the strip of material to form a closed loop with the strip of material with the at least one surface toward the interior of the closed loop. The mechanical connector receives the first end of the strip of material from a first direction in a recess being formed with a plurality of spikes upon which the strip of material is impaled and secured. The electrically conductive inner piece has a slot through which the second end of the strip of material is passed. The strap further has an adjustment mechanism secured to the second end of the strip of material and to the strip of material intermediate the mechanical connector for adjustably holding the strip of material in the closed loop. The body strap further has an electrical connection mechanism coupled to the strip of material for making electrical contact with the at least one conductive surface and for providing a connection point for an electrical cable capable of connecting the conductive body strap to ground. Preferably, the electrically conductive inner piece makes electrical contact with the at least one surface of the first end of the strip of material and also makes electrical contact with the at least one surface of the strip of material where the strip of material passes through the slot in the electrically conductive inner piece providing 360 degree electrical continuity. Preferably, the adjustment mechanism comprises an eight-ring. Preferably, the inner piece of the mechanical connector is a metallic plate and is secured by means of a metallic stud formed to receive a snap connector the metallic plate and the metallic stud forming the electrical connection mechanism.

BRIEF DESCRIPTION OF THE DRAWINGS

The foregoing advantages, construction and operation of the present invention will become more readily apparent from the following drawings and accompanying description in which.

DESCRIPTION OF THE PREFERRED EMBODIMENTS

Figure 1:
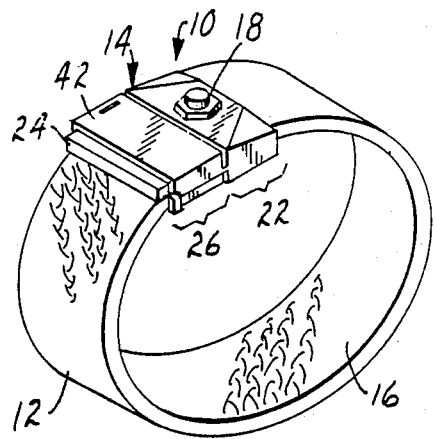
FIG. 1 illustrates an isometric view of the body strap of the present invention.

The adjustable, electrically conductive body strap 10 is illustrated in FIG. 1. The body strap 10 is formed into a closed loop designed to fit snugly around a portion of the body, e.g., a wrist or an ankle. The loop is formed by a strip of material 12 formed into a loop by connector 14. Connector 14 forms both the mechanical connection holding both ends of the strip of material 12 and the electrical connection mechanism providing a point for external connection of the body strap 10 to a ground potential. The interior surface 16 of the strip of material 12 is electrically conductive and should intimately contact the skin of the individual wearer of the body strap 10 when it is in position. Thus, electrostatic charges accumulating on the person of the wearer can be transported from the skin of the wearer to the conductive interior surface 16 of the body strap 10 transported to connector 14 and made available for conduction to ground through provision for connecting a grounding cord such as cord connector 18. Strip of material 12 may be formed of any suitable elastomeric electrically conductive material such as a fabric to form the band portion of the body strap 10. In a preferred embodiment, strip of material 12 is a knit fabric containing both elastomeric and electrically conductive fibers as described in Christiansen et al. Optionally, however, strip of material 12 could also be constructed from a stretch weave material such as is described in Breidegam. A first end 20 of the strip of material 12 is mechanically secured in a first part 22 of connector 14. The second end 24 of the strip of material 12 is adjustably secured in a second part 26 of connector 14.

Figure 4:
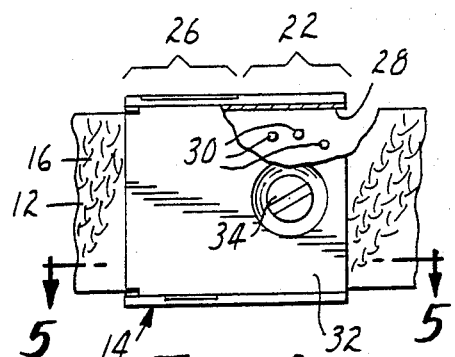
FIG. 4 illustrates a cutaway bottom view of the alternative mechanical connector.
Figure 2:
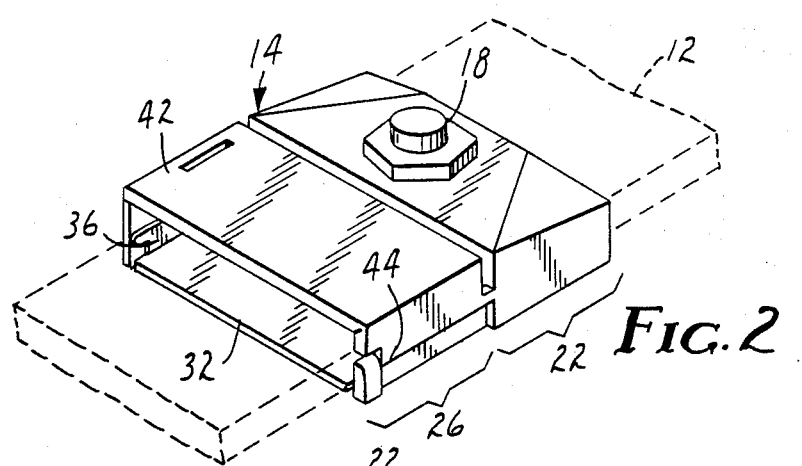
FIG. 2 illustrates a closeup of an alternative mechanical connector in a closed position.
Figure 3:
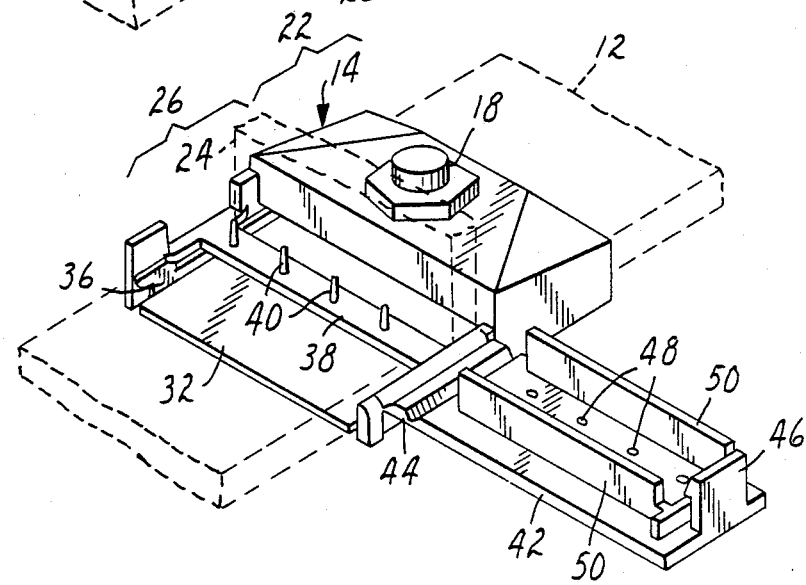
FIG. 3 illustrates a closeup of the alternative mechanical connector an open position.

The details of connector 14 are more readily illustrated in FIGS. 2 and 3. The first end 20 of the strip of material 12 is secured in the first part 22 of the connector 14. Secured in this manner the first end 20 is semi-permanently secured in that only disassembly of connector 14 can release first end 20 of the strip of material 12 from the connector 14. It is anticipated that body strap 10 can be shipped from the factory with the first end 20 of the strip of material 12 semi-permanently secured in the first part 22 of connector 14. This can be shown in better detail in FIG. 4 where the first end 20 and the strip of material 12 is formed into a recess 28 of the first part 22 of the connector 14. There the strip of material 12 is impaled upon a plurality of spikes 30 designed to secure first end 20 the strip of material 12 within the connector 14 when metallic back plate 32 which is secured in the connector 14 through a stud 34 and its cord connector 18 forming a snap connector. Stud 34 as well as cord connector 18 are metallic allowing for electrical conductivity from the interior surface 16 of the strip of material 12 to cord connector 18 and, of course, subsequently by external cord (not shown) to a ground potential. Metallic back plate 32 also preferably contacts the interior surface 16 of the second end 24 of the strip of material 12 to provide for full 360 degree electrical conductivity around body strap 10.

Figure 5:
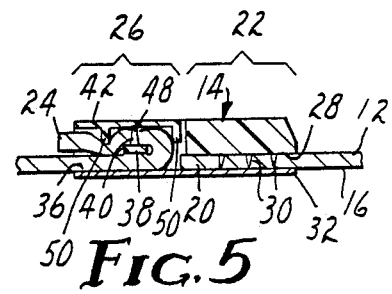
FIG. 5 illustrates a cross-section of the alternative mechanical connector in a closed position.

Again referring to FIGS. 2 and 3, the second end 24 of the strip of material 12 is placed in the recess 36 in the second part 26 of connector 14. The second part 26 of connector 14 contains a transverse bar 38 upon which are mounted a plurality of spikes 40 extending outwardly from the transverse bar 38. The second end 24 of the strip of material 12 is passed under transverse bar 38 and pulled up on the far side of transverse bar 38 until the strip of material 12 is securely tightened around the body part with which it is to be utilized. When the strip of material 12 is suitably tight, the second end 24 of the strip of material 12 is then folded back over the top of transverse bar 38 and impaled upon spikes 40. Hinged cover 42 connected to the second part 26 of connector 14 by hinge 44 along one side, may then be closed over the top of the second end 24 of the strip material 12 and secured with a hook 46 securing hinged cover 42 in place and in turn securing the second end 24 of the strip of material 12 in the connector 14. The second end 24 of the strip of material 12 may be trimmed after the strip of material 12 is impaled upon spikes 40 and either before or after hinged cover 42 is secured in a closed position as illustrated in FIG. 2. Such trimming will prevent the existence of an electrically conductive surface on the exterior of the body strap 10. Preferably, hinged cover 42 contains a plurality of recesses 48 which cooperate with and receive the tips of spikes 40 when hinge cover 42 is in a closed position. The receiving of the tip of spikes 40 in recesses 48 will help prevent spikes 40 from bending, and subsequent release of the strip of material 12 from connector 14. Also preferably, hinged cover 42 has transverse ridges 50 so on one or both sides of transverse bar 38 to force the strip of material 12 into more intimate electrical contact with back plate 32 as can be illustrated from the cross-sectional view of FIG. 5. FIG. 5 also illustrates the impaling of the strip of material 12 upon spikes 30 and 40 as well as the electrical contact between back plate 32 and both the first end 20 and the second end 24 of the strip of material 12 forming full 360 degree electrical continuity around body strap 10. FIG. 5 illustrates the second end 24 of the strip of material 12 having been trimmed with a short portion of the second end 24 extending beyond the edge of hinged cover 42. Optionally, and preferably, second end 24 of the strip of material 12 will be trimmed at least flush with the edge of hinged cover 42 so that no electrically conductive surface is present on the exterior surface of body strap 10. Also preferably, the second end 24 of the strip of material 12 is not trimmed so short that some material is left to allow for a small amount of unraveling. In a preferred embodiment, the material forming connector 14 except for back plate 32, stud 34 and cord connector 18, is constructed from a plastic material preferably one that is static dissipative. In general, a material is static dissipative if it has a surface resistivity of between $10^8$ and $10^{14}$ ohms per square. Examples of material which could be utilized and which are static dissipative include hygroscopic nylon and carbon loaded polypropylene. As can be seen from examining FIGS. 2, 3 and 5 the second end 24 of the strip of material 12 is secured in connector 14 not only by spikes 40 and hinged cover 42 but also by the tortuous path in which the fabric is forced to take when passed first under and then back over transverse bar 38.

The hinged cover 42 holds the fabric 12 onto spikes 40. Further, transverse ridges 50 assist in holding the fabric 12 onto spikes 40 and help form the tortuous path.

Figure 6:
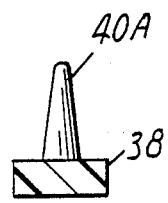
FIG. 6 illustrates one embodiment of spikes utilized in the alternative mechanical connector.
Figure 7:
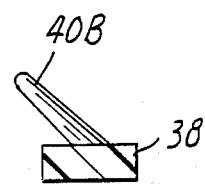
FIG. 7 illustrates another embodiment of the spikes used in the alternative mechanical connector.
Figure 8:
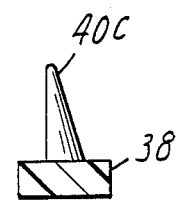
FIG. 8 illustrates another embodiment of the spikes used in the alternative mechanical connector.

FIGS. 6, 7 and 8 are cross-sections illustrating various optional profiles of spikes 40 taken from a side view. In FIG. 6, spike 40A is of conical shape which is probably the most economical to manufacture and will provide an adequate job of securing strip of material 12 for most purposes. However, severe loading upon spike 40A will tend to lead toward the strip of material 12 rising up toward the end of spike 40A which results in larger lateral forces against spike 40 then otherwise would be encountered. Accordingly, spike 40C is illustrated in FIG. 8 is preferred. Spike 40C is also of conical shape but has a zero draft, i.e., vertical side, facing the extreme second end 24 of the strip of material 12. Spike 40C with one zero draft side is still economically manufacturable and since the side of the spike 40C which is loaded is vertical strip of material 12 will not tend to ride up toward the tip of the spike 40C and, thus, the lateral force on 40C will not be concentrated at its tip but rather more evenly over the entire length of spike 40C. This results in lower lateral forces on the tip of spike 40 than might otherwise be achieved with spike 40A as illustrated in FIG. 6. If still more lateral loading resistance is desired, then spike 40B as illustrated in FIG. 7 may be utilized. Spike 40B is angled toward the extreme end 24 of strip of material 12, in this case, 45 degrees, so that any lateral force on spike 40B will result in the strip of material 12 being forced more deeply onto to spike 40B and, thus, a more secure environment is provided. However, spike 40B probably is more difficult to manufacture.

Figure 9:
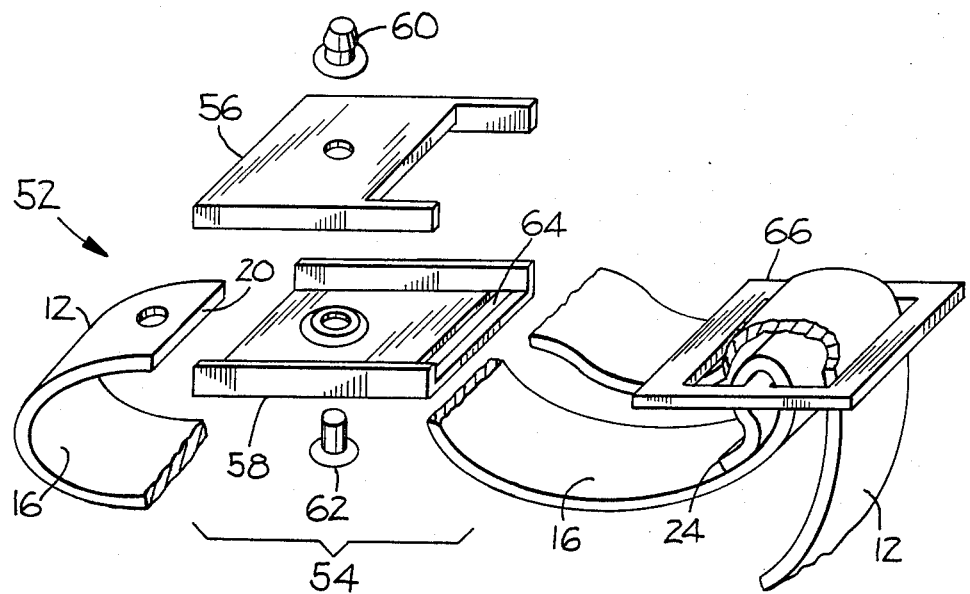
FIG. 9 illustrates an exploded view of the mechanical connector and adjustment mechanism of the adjustable, conductive body strap of the present invention.

While FIGS. 1–8 have illustrated and described adjustable, electrically conductive body straps in general, and have described, in particular, a detailed example of one way in which an adjustable conductive body strap may be constructed, FIG. 9 illustrates the adjustable, conductive body strap 52 of the present invention. A mechanical connector 54 is formed from an outer piece 56 and an inner piece 58. The outer piece 56 and the inner piece 58 are secured together by means of a snap connector 60 and stud 62. Since outer piece 56 is on the exposed exterior surface of the adjustable, conductive body strap 52, outer piece 56 is constructed from an electrically insulative material such as a plastic material, and preferably from nylon or static dissipative plastic. Since inner piece 58 is on the interior surface of the adjustable conductive body strap 52, inner piece 58 is constructed from an electrically conductive material, such as stainless steel or another metal. Inner piece 58 contacts the skin of the wearer and provides an additional electrical contact point from the adjustable conductive body strap 52 to the wearer. The first end 20 of the strip of material 12 is received into one side of mechanical connector 54 from a first direction by a recess formed by the joining of outer piece 56 and inner piece 58. Having been so received the first end 20 of strip of material 12 is held in place, alternatively, by stud 62, by one or more spikes similar to spikes 30 illustrated in FIG. 4 (not shown), or both. Secured in this manner, the inner conductive surface 16 of the strip of material 12 contacts the electrically conductive inner piece 58. A slot 64 on the other side of inner piece 58 allows for second end 24 of the strip of material to pass, first over and then under inner piece 58 with inner piece 58 making electrical contact with the electrically conductive surface 16 of the strip of material 12. The second end 24 of strip of material 12 is then secured back to itself by an eight-ring 66. Since the eight-ring 66 is exposed to the exterior of the adjustable, conductive body strap 52, it is preferred that it be constructed of an electrically insulative material, again such as a plastic material, preferably nylon or static dissipative plastic. The second end 24 of the strip of material 12 is wrapped around the central member of eight-ring 66 and secured, by any suitable mechanism, such as stitching, to itself firmly securing the second end 24 of the strip of material 12 to the eight-ring 66. The strip of material 12, having been passed between the center leg and the two outer legs of eight-ring 66, then provides a readily readjustable mechanism whereby the user of the adjustable conductive body strap 52 may resize the adjustable conductive body strap 52 in a readily efficient manner. Since there are no free ends of the strip of material 12 exposed following the strip of material 12 being secured in mechanical connector 54, there is no danger of the electrically conductive surface 16 of the strip of material 12 being left exposed to the exterior of the adjustable conductive body strap 52. Snap 60 along with stud 62 form the electrical connection mechanism whereby an electrical ground cable may be connected to snap 60 and the adjustable conductive body strap 52 may be then connected to an electrical ground. Because inner piece 58 is electrically conductive and makes electrical contact to both the first end 20 and the electrically conductive surface 16 of the strip of material 12 near second end 2, dual parallel paths for the drainage of an accumulated electrostatic charge are provided. The adjustable, conductive body strap has full 360 degree electrical continuity and near full 360 degree electrical skin contact with the only exception being the portion between slot 64 and eight-ring 66 which is a reasonable tradeoff for the elimination of any exposure of the conductive surface 16 of strip material 12 and for the readily readjustable feature of eight-ring 66.

Thus, it can be seen that there has been shown and described a novel adjustable, conductive body strap. It is to be recognized and understood, however, that various changes, modifications and substitution in the form and of the details of the present invention may be made by those skilled in the art without departing from the scope of the following claims.

What is claimed is:

1. An adjustable, conductive body strap, comprising:
   a strip of material having a first end and a second end, said strip of material being electrically conductive on at least one surface, being elastomerically extensible in its longitudinal direction, and being of at least a length to enable said strip of material to encircle a body part;
   an electrically insulative outer piece;
   an electrically conductor inner piece;
   said outer piece and said inner piece being secured together to form a mechanical connector receiving said first end and said second end of said strip of material to form a closed loop with said strip of material with said at least one surface toward the interior of said closed loop;
   said mechanical connector receiving said first end of said strip of material from a first direction in a recess being formed with a plurality of spikes upon which said strip of material is impaled and secured;
   said electrically conductive inner piece having a slot through which said second end of said strip of material is passed, said electrically conductive inner piece making electrical contact with said at least one surface of said first end of said strip of material and also makes electrical contact with said at least one surface of said strip of material where said strip of material passes through said slot providing 360 degree electrical continuity;
   adjustment means secured to said second end of said strip of material and to said strip of material intermediate said mechanical connector for adjustably holding said strip of material in said closed loop; and
   electrical connection means coupled to said strip of material for making electrical contact with said at least one conductive surface and for providing a connection point for an electrical cable capable of connecting said conductive body strap to ground.

2. An adjustable, conductive body strap as in claim 1 wherein said adjustment means comprises an eight-ring.

3. An adjustable, conductive body strap as in claim 1 wherein said inner piece of said mechanical connector is a metallic plate and is secured by means of a metallic stud formed to receive a snap connector, said metallic plate and metallic stud forming said electrical connection means.

4. An adjustable, conductive body strap as in claim 3 wherein said metallic stud is threaded and secured with a cooperating threaded member.

* * * * *